United States Patent [19]

Hudson, deceased et al.

[11] 4,419,293

[45] Dec. 6, 1983

[54] ALIPHATIC SOLVENT COMPATIBLE ISOCYANATES

[75] Inventors: George A. Hudson, deceased, late of Venetia, Pa., by Richard L. White, administrator; Helmut F. Reiff, Leverkusen, Fed. Rep. of Germany

[73] Assignee: Mobay Chemical Corporation, Pittsburgh, Pa.

[21] Appl. No.: 282,206

[22] Filed: Jul. 10, 1981

[51] Int. Cl.$^3$ .......................................... C07C 127/24
[52] U.S. Cl. .................. 260/453 AB; 260/453 SP; 525/127; 528/59
[58] Field of Search ............... 260/453 AB, 453 SP; 528/59; 525/127

[56] References Cited

U.S. PATENT DOCUMENTS

| | | | |
|---|---|---|---|
| 3,124,605 | 3/1964 | Wagner | 260/453 |
| 3,201,372 | 8/1965 | Wagner | 260/77.5 |
| 3,358,010 | 12/1967 | Britain | 260/453 AB |
| 3,789,037 | 1/1974 | Miller | 260/16 |

OTHER PUBLICATIONS

Polyurethanes: Chemistry & Technology, vol. II Technology Saunders & Fritsch, 1964, pp. 468–477.

*Primary Examiner*—Dolph H. Torrence
*Attorney, Agent, or Firm*—Gene Harsh; Lawrence S. Pope; Thomas W. Roy

[57] ABSTRACT

The present invention relates to a modified polyisocyanate having improved compatibility with aliphatic hydrocarbon solvents comprising the reaction product of (a) an aliphatic biuret isocyanate having the formula

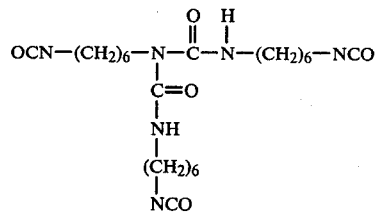

and
(b) about 0.05 to 0.5 mols per equivalent of isocyanate of an aliphatic monohydroxy alcohol having at least 8 carbon atoms.

5 Claims, No Drawings

ALIPHATIC SOLVENT COMPATIBLE ISOCYANATES

FIELD OF THE INVENTION

This invention relates to aliphatic light stable isocyanates which have been modified to have improved compatibility with aliphatic solvents and to a method of producing such isocyanates.

BACKGROUND OF THE INVENTION

It is well known that isocyanates may be added to alkyd resins to improve both the curing behavior and the properties of the cured coating. The preparation and use of urethane oils of this type are extensively discussed at pages 468 to 477 of *Polyurethanes: Chemistry and Technology*, Volume II, Technology, Saunders and Frisch, Interscience 1964. It is also known that aliphatic isocyanates impart superior light stability (resistance to yellowing, particularly on exposure to sunlight) as compared to aromatic isocyanates. A class of isocyanates which has found particular favor for coating applications are the biuret containing aliphatic or cycloaliphatic isocyanates especially the tris (isocyanato alkane) biurets such as those disclosed in U.S. Pat. Nos. 3,124,605 and 3,201,372. It has been found desirable to add such isocyanates to alkyd resin systems containing aliphatic solvents such as those used in the auto refinishing industry. Unfortunately, while these biuret isocyanates including the popular tris (isocyanato alkane) biurets exhibit some degree of compatibility with the alkyd resins themselves, they display a high degree of incompatibility with the aliphatic solvents normally used in such systems. Since these solvents are both effective and economical in such systems, it was felt that the compatibility of the aliphatic biuret isocyanates would have to be improved if they were to find practical utility in these systems.

SUMMARY OF THE INVENTION

It has been discovered that light stable aliphatic and cycloaliphatic biuret containing polyisocyanates can be modified to be more compatible with apolar solvents by reacting them with about 0.05 to 0.5 mols per equivalent of isocyanate of aliphatic or cycloaliphatic monohydroxy alcohols with at least 8 carbon atoms. The reactants should also be selected as to give an adduct mixture with an isocyanate content of between about 4 and 19 weight percent. It is preferred to use about 0.15 to 0.30 mols of alcohol. It is also preferred to use alcohols with between 14 and 30, most preferably between 14 and 20 carbon atoms. The reactants are preferably selected so as to give the adduct mixture an isocyanate content of between about 5 and 18 weight percent, most preferably between about 8 and 15 weight percent. These alcohols should be free of any substituents or bonds having a polarity greater than an aliphatically or cycloaliphatically bound isocyanate group. Included among these excluded groups are ester, ether, biuret, urea and urethane bonds.

Included among the isocyanate adduct mixtures of the present invention are those which are the reaction products of polyisocyanates of the formula:

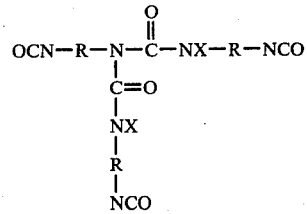

wherein R is the isocyanate free residue of an aliphatic or cycloaliphatic diisocyanate and X represents H or

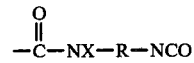

with about 0.05 to 0.5 mols per equivalent of isocyanates of an aliphatic or cycloaliphatic monohydric alcohol with at least 8 carbon atoms. The proportion of X having the meaning H and the amount of alcohol are adjusted to give the adduct mixture an isocyanate content of about 4 to 19 weight percent, preferably 5 to 18 weight percent and most preferably 8 to 15 weight percent. This proportion should also be adjusted so that the adduct mixture has an isocyanate functionality in excess of 2. Both the proportion of X having the meaning

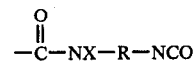

and the number of carbon atoms in the alcohol should be controlled such that the adduct mixture is soluble in common isocyanate solvents.

DETAILED DESCRIPTION OF THE INVENTION

The biuret containing polyisocyanate and the monohydric alcohol may be reacted under any thermal and catalytic conditions which give rise to the formation of urethane and/or allophanate bonds. The temperature should be sufficiently high to effect reaction within commercially acceptable times but low enough to avoid significant degradation of the polyisocyanate or the alcohol such as by destruction of the biuret bonds of the polyisocyanate. Suitable reaction conditions including temperatures and catalysts are well known to those skilled in the art and a useful compilation is contained in *Polyurethanes: Chemistry and Technology*, Volume I Chemistry, Saunders and Frisch, Interscience, 1962.

In a preferred embodiment, the reaction conditions are such as to favor allophanate as opposed to urethane bonds. Such conditions are well known to those skilled in the art, and some suitable catalysts are listed in *Polyurethanes: Chemistry and Technology*, Volume I. Among those are Pb, Co and Zn compounds such as lead naphthenate, lead 2-ethylhexanoate, lead linoresinate, cobalt naphthenate, cobalt 2-ethylhexanoate, cobalt linoresinate and zinc 2-ethylhexanoate.

The alcohol isocyanate adduct may be formed in the presence of any of the catalysts known to promote hydroxyl isocyanate reactions. A number of suitable catalysts are discussed at pages 161 to 173 of *Polyurethanes: Chemistry and Technology*, Volume I. Some suitable catalysts and other reaction conditions for reacting hydroxyl bearing compounds and biuret bond containing polyisocyanates are discussed in U.S. Pat. No. 3,201,372, incorporated herein by reference.

The most preferred embodiment is conducting the polyisocyanate addition reaction at ambient temperatures or above in the absence of any catalysts, e.g. room temperature to about 70° C. The absence of catalysts avoids the necessity of subsequently inactivating the catalyst.

The alcohol isocyanate adduct may be formed in substance or in the presence of suitable solvents. Suitable solvents should be inert to isocyanate groups, i.e., they should not contain any hydrogen groups readily reactive with NCO groups.

The adduct mixture may also be prepared by reacting the monohydroxy alcohols with the diisocyanate used to form the biuret polyisocyanate either before the formation of the biuret or simultaneously with the biuret formation.

The polyisocyanate may be any light stable biuret containing isocyanate with an average functionality in excess of 2. The light stability implies that the isocyanate groups will be either aliphatically or cycloaliphatically bound. The isocyanate free residue may be branched or linear and may carry substituents such as halogen, $NO_2$, an aryl group, an alkoxy group, an alkyl group or other groups which are inert to isocyanate groups. The polyisocyanate molecule should not carry any hydrogen atoms which are reactive with isocyanates such as hydroxyl or amine hydrogens.

The polyisocyanates may be prepared by methods well known to those skilled in the art and suitable methods of preparation are described in U.S. Pat. Nos. 3,124,605; 3,358,010 and 4,051,165, all of which are incorporated herein by reference. All of the biuret polyisocyanates described in these patents and all of the biuret polyisocyanates prepared from the starting diisocyanates described in these patents are suitable for the present invention provided that all their isocyanate groups are aliphatically or cycloaliphatically bound. Included among the suitable starting diisocyanates to prepare the biuret polyisocyanates are ethylidene diisocyanate, transvinylene diisocyanate, 1,3-bis(-γisocyanatopropoxy)-2-methyl-2-propyl propane, tetramethylene diisocyanate, pentamethylene diisocyanate, hexamethylene diisocyanate, 1,3-cyclopentylene diisocyanate, 1,4-cyclohexylene diisocyanate, 1,2-cyclohexylene diisocyanate, hexahydroxylene diisocyanate, 4,4'-dicyclohexyl diisocyanate, 1,2-di(isocyanatomethyl)-cyclobutane, 1,3-bis-(isocyanato-propoxy)-2,2-dimethylpropane, 1,3-bis-(isocyanatopropyl)-2-methyl-2-propylpropane, 1-methyl-2,4-diisocyanatocyclohexane, 1-methyl,2-6-diisocyanatocyclohexane, b-(4-isocyanatocyclohexyl)-methane, 1-4-diisocyanatocyclohexane and 1,3-diisocyanatocyclohexane, m- and p-xylylene diisocyanate, isophorone diisocyanate and 2,6-diisocyanatocaproic acid ester.

Particularly preferred aliphatic, cycloaliphatic and araliphatic diisocyanates are hexamethylene diisocyanate, the isomeric mixture of 1-methyl-2,4-diisocyanatocyclohexane and 1-methyl-2,6-diisocyanatocyclohexane, bis-(4-isocyanatocyclohexyl)-methane, m- and p-xylene diisocyanate, isophorone diisocyanate, methyl-substituted hexamethylene- and pentamethylene diisocyanate and 2,6-diisocyanatocaproic acid ester.

The most preferred diisocyanates are unsubstituted alkyl diisocyanates, particularly those with 4 to 8 carbon atoms. Especially preferred of these is hexamethylene diisocyanate.

Particularly preferred biuret polyisocyanates are those of the formula:

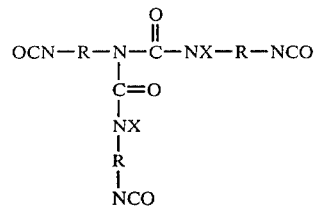

wherein R is an aliphatic or cycloaliphatic residue with only alkyl, alkoxy or no substituents, especially an alkyl or cycloalkyl residue and most preferably —(CH$_2$)$_6$— and X represents H or

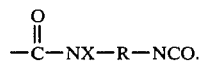

The alcohol may be any aliphatic or cycloaliphatic monohydroxy compound which has at least 8 carbon atoms and an aliphatically or cycloaliphatically bound primary or secondary hydroxyl group. The alcohol should not have any groups as integral bonds or substituents which tend to impart polarity to its molecule such as ether, ester, urea, urethane, or biuret bonds or aromatic rings. The alcohol preferably has between 14 and 30 carbon atoms and most preferably between 14 and 20 carbon atoms. It is preferred that the alcohol contain no groups which would increase the polarity of the alcohol molecule to any significant extent compared to a similar molecule without such a group. The polarity can be measured, among other methods, by determining the compatibility with apolar solvents such as straight-chained or branched alkyls. The most preferred alcohol residues are straight-chained or branched alkyls, especially the straight-chained. It is preferred that the alcohols be soluble in aliphatic solvents.

The compatibility of the adduct mixtures of the present invention with apolar solvents is determined by dissolving the adduct mixture in a suitable solvent and titrating the apolar solvent into the solution until some precipitation occurs, normally indicated by cloudiness. The solvent may be any solvent in which the biuret polyisocyanate alcohol adduct mixture has a reasonable degree of solubility. Among the more common suitable solvents are ethylene glycol monoethyl ether acetate, xylol, methylethylketone, and the like. Of particular interest are those solvent systems which have less than 20 percent by volume of photochemically reactive solvents and particularly those which meet the standards of Rule 66 of California's air pollution code. The particular solvent system in which the compatibility testing is performed is felt to have some effect on the results but not on the relative rankings of polyisocyanates tested, i.e. a more compatible polyisocyanate will remain so regardless of the solvent system although its absolute compatibility may change. The titrant may be any apolar solvent miscible with the solvent system. Of particular interest are those apolar solvents typically used with alkyd resins such as aliphatic solvents. Among these are naphtha, hexane, heptane and mineral spirits.

In the examples which follow, heptane was chosen as the titrant because it is readily available in reagent purity and it is believed to be fairly representative of the apolar solvents. Subsequent testing with commercially available alkyd systems (resin and solvents) verified the results of the heptane titrations. In each case, a 50 gram sample of the polyisocyanate system to be evaluated was diluted down to a 40 weight percent solids content with toluene. In most cases, the polyisocyanate was already present as a solution at some higher solids content.

EXAMPLES I–VI

The biuret polyisocyanate solution of Comparison Example I was reacted with the various reactants indicated in Table I and sufficient xylol was added to maintain the solids at 75% (Examples I, II and V) or the polyisocyanate was initially solvent free and the adduct was formed in sufficient solvent to make a 50% toluene solution (Examples III, IV and VI). In each case, the

| Identification | Polyisocyanate | Total Solids Before Dilution | Solvent System | Weight % NCO | Heptane Tolerance |
|---|---|---|---|---|---|
| Comparison Example I | Biuret tris-isocyanate of hexamethylene diisocyanate | 75% | CA[1]/xylol 1:1 | 16.2 | 3.4 ml |
| Example I | Adduct Comparison Ex. I and 0.1 mol % octadecanol | 75% | CA/xylol | 12.7 | 7.8 ml |
| Example II | Adduct Comparison Ex. I and 0.1 mol % tetradecanol | 75% | CA/xylol | 12.9 | 6.2 ml |
| Example III | Adduct Comparison Ex. I and 0.1 mol % n-decanol | 50% | Toluene | — | 6.4 ml |
| Example IV | Adduct Comparison Ex. I and 0.1 mol % trimethylnonanol | 50% | Toluene | — | 6.7 ml |
| Example V | Adduct Comparison Ex. I and 0.1 mol % hexadecanol | 75% | CA/xylol | 12.7 | 7.8 ml |
| Example VI | Adduct Comparison Ex. I and 0.1 mol % 2-ethylhexanol | 50% | Toluene | — | 5.8 ml |
| Comparison Example II | Adduct Comparison Ex. I and 0.1 mol % nonyl phenol | 75% | CA/xylol | 13.2 | 4.3 ml |
| Comparison Example III | Adduct Comparison Ex. I and 0.1 mol % cyclohexanol | 50% | Toluene | — | 4.8 ml |
| Comparison Example IV | Adduct Comparison Ex. I .05 mol % propylene glycol and .05 mol % tetradecanol | 75% | CA/xylol | 13.2 | 3.4 ml |
| Comparison Example V | Adduct Comparison Ex. I .05 mol % esterdiol[3] and .05 mol % tetradecanol | 75% | CA/xylol | 13.4 | 3.7 ml |
| Comparison Example VI | Adduct Comparison Ex. I and 0.13 mol % hexyl-cellosolve ($C_8$) | 75% | CA/xylol | — | 4.7 ml |
| Comparison Example VII | Adduct Comparison Ex. I and 0.12 mol % hexyl-carbitol ($C_{10}$) | 75% | CA/xylol | — | 5.2 ml |
| Example VII | Adduct Comparison Ex. I and 0.2 mol % hexadecanol | 50% | xylene | 6.9 | 16.0 ml |
| Example VIII | Adduct Comparison Ex. I and 0.15 mol % hexadecanol | 50% | xylene | 7.7 | 11.0 ml |
| Example IX | Adduct Comparison Ex. I and 0.1 mol % hexadecanol | 50% | xylene | 8.6 | 7.0 ml |

[1]CA is an abbreviation for ethylene glycol monoethyl ether acetate
[2]Trimethylnonanol is more precisely 2,6,8-trimethylnonanol-4
[3]Ester diol has the structure 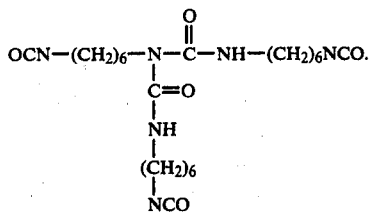

COMPARISON EXAMPLE I

Comparison Example I is a biuret polyisocyanate having the idealized structure:

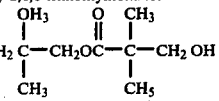

It is a 75 weight percent solution in a 1:1 solvent blend of ethylene glycol monoethyl ether acetate and xylol with an NCO equivalent weight of 255.

reaction was carried out until the NCO value was at or below the theoretical amount based on the reactants.

COMPARISON EXAMPLES II–VII

These examples were conducted in a manner similar to Examples I–VI except that the NCO content was not determined in Comparison Examples VI and VII. In these examples, the reactants were cooked at 60° C. for sixteen hours and after an initial heptane tolerance determination 0.01 weight percent of dibutyltin dilaurate was added. On redetermination, no significant change in heptane tolerance was noted.

EXAMPLES VII–IX

These examples were run in a manner similar to Examples I and VI except that the initial polyisocyanate was solvent free and the final adduct was prepared in sufficient solvent to give a 50% solution in xylol.

EXAMPLE X

The adducts of Examples VII–IX were evaluated for their compatibility with commercial alkyd resin systems, Sherwin Williams SA4892 and Kem Finishing Clear No. 7. The alkyds are medium oil length drying alkyds based on phthalic anhydride and soy bean oil, tall oil, and unsaturated fatty acids. The solvent system consists of apolar aliphatic solvents. The Example VII adduct is completely compatible, that of Example VIII is marginally compatible, and that of Example IX is incompatible. The compatibility was determined by combining 4 g of the 50% xylol solution with 100 g of the alkyd system which is approximately 60% solids in mainly mineral spirits and evaluating the cloudiness of the resultant mixture. Slight cloudiness indicated marginal compatibility and a clear mixture good compatibility.

EXAMPLE XI

The adducts of Examples VII and VIII are combined with Sherwin Williams Kem Transport Enamel White (FI-W-4356) which is similar to the alkyd systems of Example X except it contains pigmentation. The cured coatings were compared to that obtained from the isocyanaurate trimer of isophorone diisocyanate with the idealized structure:

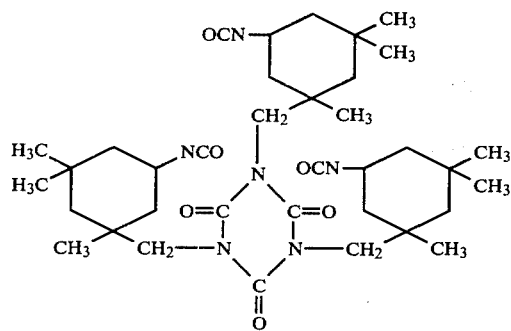

This trimer is known to have very good compatibility in alkyd systems and is being commercially promoted as a modifier for such systems.

| Drying Rates | Example VII Adducts | Example VIII Adducts | Isocyanurate Trimer |
|---|---|---|---|
| Tack Free Time (Sand) | 1.5 hours | 2 hours | 4 hours |
| Tape Time | 4.0 hours | 4 hours | 5 hours |
| After 10 Days R.T. Cure | | | |
| Impact, Reverse | 160 | 160 | 30 |
| Direct | 160 | 160 | 120 |
| Pencil Hardness | HB | HB | B |
| MEK Double Rubs | 100 | 100 | 75 |
| | Softened | Softened | Failed |
| After 3 Weeks R.T. Cure | | | |
| Impact, Reverse | 140 | 140 | 4 |
| Direct | 160 | 160 | 50 |
| Pencil Hardness | HB | HB | HB |
| MEK Double Rubs | 100 | 100 | 100 |
| | Softened | Softened | Softened |
| Gasoline Resistance, 4 hours | Sl. Stain Sl. Softd. | Sl. Stain Sl. Softd. | Sl. Stain Sl. Softd. |

As the above experiments demonstrate, the reaction of biuret polyisocyanates with small amounts of long chain alcohols will yield products having both high NCO content and good compatibility with apolar solvents such as those used in alkyd resin systems. The compatibility of these adducts with aliphatic solvents such as heptane is a good predictor of compatibility with commercial alkyd resin systems and these adducts can be combined with such systems to yield high quality coatings.

However, if the alcohol contains or introduces polarity inducing groups, the improved compatibility may be lost. In Comparison Example II a benzene ring is contained in Comparison Examples IV and V urethane groups are introduced via the difunctional alcohol and in Comparison Examples VI and VII ether groups are included.

In the present invention, it is preferred that the adduct have a minimum heptane tolerance of about 12 ml. As can be seen from Example X, this should ensure good compatibility with commercial alkyd systems.

Although the invention has been described in detail in foregoing for the purpose of illustration, it is to be understood that such detail is solely for that purpose and that variations can be made therein by those skilled in the art without departing from the spirit and scope of the invention except as it may be limited by the claims.

What is claimed is:

1. A modified polyisocyanate having improved compatibility with aliphatic hydrocarbon solvents comprising the reaction product of (a) an aliphatic biuret isocyanate having the formula

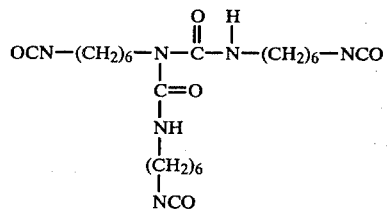

and (b) about 0.05 to 0.5 mols per equivalent of isocyanate of an aliphatic monohydroxy alcohol having between 14 and 30 carbon atoms.

2. A modified aliphatic isocyanate having a heptane compatibility of at least about 6 ml when present as 40% toluene solution at room temperature and having an NCO content of at least about 10 weight percent based on solids comprising the reaction product of tris-(hexylisocyanato) biuret and an aliphatic monohydroxy alcohol having between 14 and 30 carbon atoms.

3. The modified polyisocyanate of claim 1 wherein the alcohol is a linear primary alcohol having between 14 and 20 carbon atoms.

4. A light stable polyisocyanate adduct mixture having improved compatibility with apolar solvents and having an isocyanate functionality of greater than about 2 comprising the reaction product of (a) a polyisocyanate of the formula

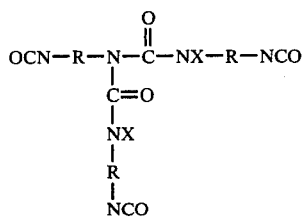

wherein R is the isocyanate free aliphatic or cycloaliphatic residue of an organic diisocyanate, and X represents H or

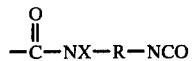

with sufficient X being H that the polyisocyanate is soluble in polar solvents, and (b) about 0.05 to 0.5 mols per equivalent of isocyanate of an aliphatic or cycloaliphatic monohydric alcohol having between 14 and 30 carbon atoms, said adduct mixture having an isocyanate content of between about 4 and 19 weight percent.

5. A process for improving the compatibility of biuret containing aliphatic or cycloaliphatic light stable polyisocyanates comprising reacting them with 0.05 to 0.5 mols per equivalent of isocyanate of an aliphatic or cycloaliphatic monohydric alcohol having between 14 and 30 carbon atoms so as to produce an adduct mixture having an isocyanate content of between about 4 and 19 weight percent.

* * * * *